(12) United States Patent
Krafft et al.

(10) Patent No.: US 8,106,246 B2
(45) Date of Patent: *Jan. 31, 2012

(54) PROCESS FOR THE MANUFACTURE OF DICHLOROPROPANOL BY CHLORINATION OF GLYCEROL

(75) Inventors: Philippe Krafft, Rhode Saint Genese (BE); Christian Franck, Sterrebeek (BE); Ivan de Andolenko, Tavaux (FR); Roger Veyrac, Louvatange (FR)

(73) Assignee: SOLVAY (Societe Anonyme), Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/051,007

(22) Filed: Mar. 18, 2011

(65) Prior Publication Data

US 2011/0172449 A1     Jul. 14, 2011

Related U.S. Application Data

(63) Continuation of application No. 12/092,178, filed as application No. PCT/EP2006/068208 on Nov. 8, 2006, now Pat. No. 7,939,696.

(60) Provisional application No. 60/734,637, filed on Nov. 8, 2005.

(51) Int. Cl.
C07C 31/34     (2006.01)
C07D 301/26    (2006.01)

(52) U.S. Cl. ........................ 568/844; 549/514
(58) Field of Classification Search .................. 549/514; 568/844

See application file for complete search history.

(56) References Cited

U.S. PATENT DOCUMENTS

| | | |
|---|---|---|
| 865,727 A | 9/1907 | Queneau |
| 2,060,715 A | 11/1936 | Arvin |
| 2,063,891 A | 12/1936 | Dreyfus |
| 2,144,612 A | 1/1939 | Lyman et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,726,072 A | 12/1955 | Hermann |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,061,615 A | 10/1962 | Viriot et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,839,169 A | 10/1974 | Moyer |
| 3,865,886 A | 2/1975 | Schindler et al. |
| 3,867,166 A | 2/1975 | Sullivan |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,173,710 A | 11/1979 | Boulet et al. |
| 4,220,529 A | 9/1980 | Daude-Lagrave |
| 4,390,680 A | 6/1983 | Nelson |
| 4,405,465 A | 9/1983 | Moore et al. |
| 4,415,460 A | 11/1983 | Suciu et al. |
| 4,499,255 A | 2/1985 | Wang et al. |
| 4,595,469 A | 6/1986 | Foller |
| 4,609,751 A | 9/1986 | Hajjar |
| 4,634,784 A | 1/1987 | Ishioka et al. |
| 4,655,879 A | 4/1987 | Brockmann et al. |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,286,354 A | 2/1994 | Bard et al. |
| 5,344,945 A | 9/1994 | Grunchard |
| 5,359,094 A | 10/1994 | Teles et al. |
| 5,445,741 A | 8/1995 | Dilla et al. |

(Continued)

FOREIGN PATENT DOCUMENTS

CN     1296003 A     5/2001

(Continued)

OTHER PUBLICATIONS

Kirk-Othmer Encyclopedia of Chemical Technology, New York, Wiley, e-book, 2000-2010, vol. 13, p. 808-837.*

(Continued)

Primary Examiner — Brian J Davis
(74) Attorney, Agent, or Firm — Oblon, Spivak, McClelland, Maier & Neustadt, L.L.P.

(57) ABSTRACT

Process for the manufacture of dichloropropanol in which glycerol is reacted with a chlorinating agent comprising hydrochloric acid in a liquid medium in equilibrium with a vapor phase and in which the condensation of a fraction exhibiting the composition of the vapor phase is prevented.

9 Claims, No Drawings

U.S. PATENT DOCUMENTS

| | | | |
|---|---|---|---|
| 5,567,359 A | 10/1996 | Cassidy et al. |
| 5,578,740 A | 11/1996 | Au et al. |
| 5,710,350 A | 1/1998 | Jeromin et al. |
| 5,731,476 A | 3/1998 | Shawl et al. |
| 5,744,655 A | 4/1998 | Thomas et al. |
| 5,779,915 A | 7/1998 | Becker et al. |
| 5,908,946 A | 6/1999 | Stern et al. |
| 5,993,974 A | 11/1999 | Fukushima et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,719,957 B2 | 4/2004 | Brady, Jr. et al. |
| 6,740,633 B2 | 5/2004 | Norenberg et al. |
| 7,126,032 B1 | 10/2006 | Aiken |
| 7,557,253 B2 | 7/2009 | Gilbeau |
| 7,584,629 B2 | 9/2009 | Sohn et al. |
| 7,615,670 B2 | 11/2009 | Gilbeau |
| 7,893,193 B2 | 2/2011 | Krafft et al. |
| 7,906,691 B2 | 3/2011 | Krafft et al. |
| 7,906,692 B2 | 3/2011 | Krafft et al. |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0150123 A1 | 8/2004 | Strofer et al. |
| 2004/0179987 A1 | 9/2004 | Oku et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0293707 A1 | 12/2007 | Wolfert et al. |
| 2008/0154050 A1 | 6/2008 | Gilbeau |
| 2008/0194847 A1 | 8/2008 | Krafft et al. |
| 2008/0194850 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2010/0032617 A1 | 2/2010 | Gilbeau et al. |
| 2010/0105862 A1 | 4/2010 | Krafft et al. |
| 2010/0105964 A1 | 4/2010 | Krafft et al. |
| 2010/0168379 A1 | 7/2010 | Krafft et al. |
| 2010/0170805 A1 | 7/2010 | Krafft et al. |
| 2010/0179300 A1 | 7/2010 | Boulos et al. |
| 2010/0179302 A1 | 7/2010 | Krafft et al. |
| 2010/0212540 A1 | 8/2010 | Bobet et al. |
| 2010/0294727 A1 | 11/2010 | Gilbeau et al. |
| 2010/0305367 A1 | 12/2010 | Borremans |
| 2010/0311942 A1 | 12/2010 | Gilbeau et al. |
| 2011/0028683 A1 | 2/2011 | Gilbeau et al. |

FOREIGN PATENT DOCUMENTS

| | | |
|---|---|---|
| CN | 101041421 | 9/2007 |
| DE | 58396 | 8/1891 |
| DE | 180 668 | 1/1906 |
| DE | 197308 C | 11/1906 |
| DE | 238341 C | 3/1908 |
| DE | 197309 | 4/1908 |
| DE | 869 193 | 3/1953 |
| DE | 1 041 488 | 10/1958 |
| DE | 1 075 103 | 2/1960 |
| DE | 30 03 819 | 8/1981 |
| DE | 216 471 | 6/1983 |
| DE | 32 43 617 | 5/1984 |
| DE | 3 721 003 | 6/1987 |
| DE | 1 226 554 | 2/1994 |
| DE | 102 03 914 | 1/2002 |
| DE | 102 54 709 | 6/2004 |
| DE | 238341 | 3/2008 |
| EP | 0 296 341 | 12/1988 |
| EP | 0 347 618 | 12/1989 |
| EP | 0 421 379 | 4/1991 |
| EP | 0 518 765 | 12/1992 |
| EP | 0 522 382 | 1/1993 |
| EP | 0 535 949 | 4/1993 |
| EP | 0 563 720 | 10/1993 |
| EP | 0 568 389 | 11/1993 |
| EP | 0 618 170 | 10/1994 |
| EP | 0 916 624 | 5/1999 |
| EP | 0 919 551 | 6/1999 |
| EP | 0 774 450 | 2/2000 |
| EP | 1 059 278 | 12/2000 |
| EP | 1 106 237 | 6/2001 |
| EP | 1 153 887 | 11/2001 |
| EP | 1 163 946 | 12/2001 |
| EP | 1 298 154 | 4/2003 |
| EP | 0 561 441 | 9/2003 |
| EP | 1 411 027 | 4/2004 |
| EP | 1 752 435 | 2/2007 |
| EP | 1 752 436 | 2/2007 |
| EP | 1 760 060 | 3/2007 |
| EP | 1 762 556 | 3/2007 |
| EP | 1 770 081 | 4/2007 |
| EP | 1 772 446 | 4/2007 |
| EP | 1 775 278 | 4/2007 |
| EP | 2 085 364 | 8/2009 |
| FR | 1 417 388 | 10/1964 |
| FR | 1 476 073 | 4/1966 |
| FR | 2 180 138 | 5/1973 |
| FR | 2 565 229 | 12/1985 |
| FR | 2 752 242 | 2/1998 |
| FR | 2 862 644 | 5/2005 |
| FR | 2 868 419 | 10/2005 |
| FR | 2 869 612 | 11/2005 |
| FR | 2 869 613 | 11/2005 |
| FR | 2 885 903 | 11/2006 |
| FR | 2 912 743 | 8/2008 |
| FR | 2 913 683 | 9/2008 |
| FR | 2 917 411 | 12/2008 |
| FR | 2 918 058 | 1/2009 |
| FR | 2 925 045 | 6/2009 |
| FR | 2 929 611 | 10/2009 |
| FR | 2 935 699 | 3/2010 |
| FR | 2 935 968 | 3/2010 |
| GB | 14767 A | 0/1914 |
| GB | 404 938 | 7/1932 |
| GB | 406345 | 8/1932 |
| GB | 467 481 | 9/1935 |
| GB | 541 357 | 11/1941 |
| GB | 679536 | 9/1952 |
| GB | 736641 | 7/1953 |
| GB | 799567 | 8/1958 |
| GB | 1083594 | 11/1964 |
| GB | 984 446 | 2/1965 |
| GB | 984633 | 3/1965 |
| GB | 1 387 668 | 3/1972 |
| GB | 1 286 893 | 8/1972 |
| GB | 1 414 976 | 11/1975 |
| GB | 2 173 496 | 10/1986 |
| GB | 702143 | 10/1990 |
| GB | 2 336 584 | 10/1999 |
| HU | 2002-003023 | 3/2004 |
| JP | 39-27230 | 11/1928 |
| JP | 55-041858 | 3/1980 |
| JP | 56-29572 | 3/1981 |
| JP | 56-99432 | 8/1981 |
| JP | 61-112066 | 5/1986 |
| JP | 62-242638 | 10/1987 |
| JP | 63-195288 | 8/1988 |
| JP | 2-137704 | 5/1990 |
| JP | 03-014527 | 1/1991 |
| JP | 3-223267 | 10/1991 |
| JP | 03-223267 | 10/1991 |
| JP | 04-089440 | 3/1992 |
| JP | 04-217637 | 8/1992 |

| | | |
|---|---|---|
| JP | 6-25196 | 4/1994 |
| JP | 6-184024 | 7/1994 |
| JP | 06-321852 | 11/1994 |
| JP | 8-59593 | 3/1996 |
| JP | 09-299953 | 11/1997 |
| JP | 10-139700 | 5/1998 |
| JP | 10-218810 | 8/1998 |
| JP | 2001-213827 | 8/2001 |
| JP | 2001-261308 | 9/2001 |
| JP | 2001-1261581 | 9/2001 |
| JP | 2002-02033 | 1/2002 |
| JP | 2002-038195 | 2/2002 |
| JP | 2002-363153 | 12/2002 |
| JP | 2003-81891 | 3/2003 |
| JP | 2003-89680 | 3/2003 |
| JP | 2005-007841 | 1/2005 |
| JP | 2005-097177 | 4/2005 |
| JP | 76021635 | 4/2005 |
| JP | 2007-008898 | 1/2007 |
| JP | 2009-263338 | 11/2009 |
| KR | 900006513 | 11/1987 |
| KR | 2003-29740 | 5/2003 |
| KR | 10-0514819 | 11/2004 |
| SU | 1125226 | 11/1984 |
| SU | 1159716 | 6/1985 |
| SU | 1685969 | 10/1991 |
| WO | WO 96/07617 | 3/1996 |
| WO | WO 96/15980 | 5/1996 |
| WO | WO 97/48667 | 12/1997 |
| WO | WO 98/37024 | 8/1998 |
| WO | WO 99/14208 | 3/1999 |
| WO | WO 99/32397 | 7/1999 |
| WO | WO 01/86220 | 11/2001 |
| WO | WO 02/26672 | 4/2002 |
| WO | WO 03/064357 | 8/2003 |
| WO | WO 2004/056758 | 7/2004 |
| WO | WO 2005/021476 | 3/2005 |
| WO | WO 2005/054167 | 6/2005 |
| WO | WO 2005/097722 | 10/2005 |
| WO | WO 2005/115954 | 12/2005 |
| WO | WO 2005/116004 | 12/2005 |
| WO | WO 2006/020234 | 2/2006 |
| WO | WO 2006/100311 | 9/2006 |
| WO | WO 2006/100312 | 9/2006 |
| WO | WO 2006/100313 | 9/2006 |
| WO | WO 2006/100314 | 9/2006 |
| WO | WO 2006/100315 | 9/2006 |
| WO | WO 2006/100316 | 9/2006 |
| WO | WO 2006/100317 | 9/2006 |
| WO | WO 2006/100318 | 9/2006 |
| WO | WO 2006/100319 | 9/2006 |
| WO | WO 2006/100320 | 9/2006 |
| WO | WO 2006/106153 | 10/2006 |
| WO | WO 2006/106154 | 10/2006 |
| WO | WO 2006/106155 | 10/2006 |
| WO | WO 2007/054505 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/043796 | 4/2009 |
| WO | WO 2009/077528 | 6/2009 |
| WO | WO 2009/095429 | 8/2009 |
| WO | WO 2009/121853 | 10/2009 |
| WO | WO 2010/029039 | 3/2010 |
| WO | WO 2010/029153 | 3/2010 |
| WO | WO 2010/066660 | 6/2010 |

OTHER PUBLICATIONS

Herman A. Bruson, et al., "Thermal Decomposition of Glyceryl Carbonates," Journal of the American Chemical Society, vol. 74, Apr. 1952, pp. 2100-2101.

Gibson, "The Preparation, Properties and Uses of Glycerol, Derivatives, Part III., The Chlorohydrins", 1931, Chemistry and Industry, Chemical Society, pp. 949-975.

Carre et al., "La Transformation Des Alcools Polyatomiques en Mono- et en Polychlorohydrines au Moyen du Chlorure de Thionyle," Bulletin De La Societe Chmique De France, Societe Francaise de Chemie, Paris—ISSN 0037-8968, 1931, vol. 49, No. 49, pp. 1150-1154.

Fauconner, 1888, "Preparation de l'epichlorhydrine", Bull. Soc. Chim. FR, Mo. 50, pp. 212-214.

Ullmann's Encylopedia of Industrial Chemistry, "Industrially important epoxides", 1987, 5$^{th}$ Ed., vol. A9, pp. 539-540.

Bonner et al., "The composition of constant boiling hydrochloric acid at pressures of 50 to 1220 millimeters", 1930, Journal of American Chemical Society, vol. 52, pp. 633-635.

Muskof et al., "Epoxy Resins" in Ullmann's Encyclopedia of Industrial Chemistry, 1987, 5$^{th}$ Ed., vol. A9, pp. 547-563.

Novelli, A., "The perparationf mono- and dichlorohydrins of glycerol", 1930, Anales Farmacia Bioquimica, vol. 1, pp. 8-19.

Perry's Chemical Engineers Handbook 7$^{th}$ Ed., 11$^{th}$ Section, 1997, pp. 11.1-11.118.

Perry's Chemical Engineers Handbook 7th Ed., 13th Section, 1997, pp. 13.1-13.108

Ullmann's Encyclopedia of Industrial Chemistry 5$^{th}$ Ed., vol. A23, 1993, pp. 635-636.

Ullmann's Encyclopedia of Industrial Chemistry 5$^{th}$ Ed., vol. A13, 1989, pp. 289.

Ullmann's Encyclopedia of Industrial Chemistry 5$^{th}$ Ed., vol. A11, 1988, pp. 354-360.

Application No. FR 06.05325 filed Jun. 14, 2006 by Solvay SA—priority document to EP 2007/55742 published as WO 2007/144335.

Perry's Chemical Engineers Handbook 7th Ed., 15th Section, 1997, pp. 15.1-15.47.

Application No. FR 07.53863 filed Mar. 15, 2007 by Solvay SA and published as FR 2913683—priority document to EP 2007/55742 published as WO 2007/144335.

Derwent Publications, AN 109:6092 CA, JP 62-242638, Oct. 23, 1987.

Derwent Publications, AN 1987-338139 [48], JP 62-242638, Oct. 23, 1987.

Semendyava, ND et al., 1981, Kimicheskaya Promyschlennost, Seriya: Khornaya Promysshelennost, 5, 21-2 (CA Summary) XP 002465275.

I. Miyakawa et al., Nagoya Sangyo Kagaku Kenkyusho Kenkyu Hokoku, 10, 49-52 (1957).

Han Xiu-Ying et al., Shansi Daxue Xueba Bianjibu, 2002, 25(4), 379-80.

Rudneko, EV et al., 1988, Kukokrasochnye Materialy, Ikh Pr., 4, 69-71 (CA Summary) XP 002465276.

Kirk-Othmer Encyclopedia of Chemical Technology, 1978, 3$^{rd}$ Ed. vol. 4, Blood. Coagulants and Anticoagulants to Cardiovascular Agents, p. 847-848.

K. Weissermel and H J. Arpe in Industrial Organic Chemistry, Third, Completely Revised Edition, VCH, 1997, pp. 149,275.

Industrial Bioproducts: "Today and Tomorrow," Energetics, Inc. for the U.S. Department of Energy, Office of Energy Efficiency and Renewable Energy, Office of the Biomass Program, Jul. 2003, pp. 49, 52 to 56.

Kirk Othmer Encyclopedia of Chemical Technology, Fourth Edition, 1992, vol. 2, p. 156, John Wiley & sons, Inc.

Ullmann's Encyclopedia of Industrial Chemistry, Fifth, Completely Revised Edition, 1985, vol. A13, pp. 292-293.

The Merck Index, Eleventh Edition, 1989, pp. 759-760.

Hancock, E.G., Propylene and its Industrial Derivatives, 1973, pp. 298-332.

K. Weissermel and H. J. Arpe in Industrial Organic Chemistry, Third, Completely Revised Edition, VCH 1997, pp. 149-163.

K. Weissermel and H. J. Arpe in Industrial Organic Chemistry, Third, Completely Revised Edition, VCH 1997, pp. 275-276.

Perry's Chemical Engineers Handbook, Sixth Edition, Robert H. Perry, Don Green, 1984, Section 21-44 to 21-68.

Iwanami Dictionary of Physics and Chemistry, Third edition, Ryo Midorikawa/Iwanami Shoten, Publishers, May 29, 1971, pp. 270-271, 595 and 726.

Expert Opinion on the Environment Impact Assessment Documentation Pursuant to Annex No. 5 of Act No. 100/2001 Coll,. as amended by later regulations of the project/intent combined process for the manufacture of epichlorohydrin (SPOLEK) Apr. 2005.

Berichte Der Deutschen Chemischen Gesellschaft, 1891, vol. 24, pp. 508-510.

Chemical Engineering Handbook, the 6th Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.

Product Brouchure of De Dietrich Company, Apr. 1996, pp. 3, 8 and 9 w/English translation of p. 8, left column, lines 1-4, p. 9.

Oleoline, com, Glycerine Market report, 10th Sep. 2003, No. 62.

Notification Under Act. No. 100/2001, Coll. As Amended by Act No. 93/2004, Coll. To the extent of Annex No. 4, (SPOLEK) Nov. 30, 2004.

Documentation Under Act No. 100/2001 Coll. As amended by Act No. 93/2004 Coll in the scope of appendix No. 4 (SPOLEK) Jan. 11, 2005.

Kirk Othmer Encyclopedia of Chemical Technology, Third Edition, vol. 12, 1980, pp. 1002-1005.

The Journal of the American Chemical Society, vol. XLV, Jul.-Dec. 1923, pp. 2771-2772.

Catalogue of Nittetu Chemical Engineering Ltd. (Published in Mar. 1994).

J.B. Conant et al., "Glycerol α,y-dichlorophydrin", Organic Syntheses Coll., 1941, vol. 1, p. 292-294 (5 pages).

12093 Chemicals, Chemical Daily Co., Ltd. (Published on Jan. 22, 1993) with attached English translation of relevant excerpts.

M. Schellentrager, "Untersuchungen zur oxidation Entfarbung aus gewahlter Reaktivfarbstoffe: Analyse der Abbauprodukte miteels hochauflosender LC-MS", Diisertation, XP002548413 (Jan. 1, 2006) w/Attached English Abstract.

Chemicals Guide, Chemical Daily Co., Ltd. (Published on Jun. 15, 1990) with attached English translation of relevant excerpts.

Robert T. Morrison & Robert N. Boyd, Organic Chemistry, vol. II, pp. 666 to 667 and 712 to 714 (Japanese translation), published on Jul. 10, 1970, Tokyo Kagaku Dozin Co., Ltd. (and copies of similar passages but retrieved from the English 5th Edition of the Book, 1987.

Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).

Ullmann Encyl. Industr. Chem., 5th Ed., vol. A6, (1988), pp. 401-477.

Polymer Science Dictionary, M.S.M., Elsevier Applied Chemistry, London and New York 1989, p. 86.

Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

E. Milchert et al., "Installation for the Recovery of Dichloropropanols and Epichlorohydrin from the Waste Water in Epichlorohydrin Production", Pol. J. Appl. Chem., vol. 41, p. 113-118 (1997).

Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V;—2005 p. 81/-8/5., vol. 5.

Klaus Weissermel, et al., "Industrial Organic Chemistry," (3rd Completely Revised Edition); VCH 1997. p. 93-98.

Klaus Weissermel, et al., "Industrial Organic Chemistry," (3rd Completely Revised Edition); VCH 1997. p. 276-277.

Klaus Weissermel, et al., "Industrial Organic Chemistry," (3rd Completely Revised Edition); VCH 1997. p. 347-355.

RD 436093, filed Aug. 10, 2000, Research Disclosure.

Ullmann's Encyclopedia of Industrial Chemistry, 2005, Wiley-VCH GmbH & Co., KgaA, Weinhem, pp. 8-15 and 401-477, Published online Mar. 15, 2001.

Ma Zengxin, Gan Yicui, Recovery of Polyglycerol from Residues of Synthetic Glycerol—Riyong Huaxue Gongye, 1997, 4, 21023.

Perry's Chemical Engineers Handbook, Sixth Edition, McGraw Hill Inc., (1984) Section 18.

U.S. Appl. No. 60/560,676, filed Apr. 8, 2004, Gilbeau, et al.
U.S. Appl. No. 60/734,659, filed Nov. 8, 2005, Krafft, et al.
U.S. Appl. No. 60/734,627, filed Nov. 8, 2005, Krafft, et al.
U.S. Appl. No. 60/734,657, filed Nov. 8, 2005, Krafft, et al.
U.S. Appl. No. 60/734,658, filed Nov. 8, 2005, Gilbeau, et al.
U.S. Appl. No. 60/734,635, filed Nov. 8, 2005, Krafft, et al.
U.S. Appl. No. 60/734,634, filed Nov. 8, 2005, Kraft, et al.
U.S. Appl. No. 60/734,637, filed Nov. 8, 2005, Krafft, et al.
U.S. Appl. No. 60/734,636, filed Nov. 8, 2005, Krafft, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007.
U.S. Appl. No. 13/060,421, filed Feb. 23, 2011, Balthasart, et al.
U.S. Appl. No. 13/063,230, filed Mar. 10, 2011, Krafft, et al.

W. Giger et al., "14C/12C—Ratios in Organic Matter and Hydrocarbons Extracted from Dated Lake Sediments," Nuclear Instruments and Methods in Physics Research B5 (1984), 394-397. XP-002631954.

Jurgen O. Metzger, "Fats and Oils as Renewable Feedstock for Chemistry," Eur. J. Lipid Sci. Technol. (2009), 111, 865-876. XP-002631953.

Bruce M. Bell, "Glycerin as a Renewable Feedstock for Epichlorohydrin Production. The GTE Process," Clean-Soil, Air, Water, vol. 36, No. 8, (2008) pp. 657-661. XP-002631952.

Sang Hee Lee, et al., "Direct Preparation of Dichloropropanol (DCP) from Glycerol Using Heteropolyacid (HPA) Catalysts: A Catalyst Screen Study," Catalysis Communications (9), 2008, 1920-1923.

U.S. Appl. No. 13/131,516, filed May 26, 2011, Gilbeau, et al.

\* cited by examiner

PROCESS FOR THE MANUFACTURE OF DICHLOROPROPANOL BY CHLORINATION OF GLYCEROL

REFERENCE TO PRIOR APPLICATIONS

This application is a Continuation of U.S. application Ser. No. 12/092,178, filed Apr. 30, 2008, now allowed; which is a 371 of PCT/EP06/68208, filed Nov. 8, 2006; and claims benefit of U.S. Provisional application No. 60/734,637, filed Nov. 8, 2005.

The present invention relates to a process for the manufacture of dichloropropanol in which glycerol and a chlorinating agent are reacted optionally in the presence of an organic acid, so as to obtain reaction products comprising dichloropropanol. The dichloropropanol can be separated from the other reaction products and can be subjected to a dehydrochlorination reaction, so as to manufacture epichlorohydrin. Such a process is disclosed in Application WO 2005/054167 of SOLVAY S A, the content of which is incorporated in the present application by reference. A preferred chlorinating agent is hydrogen chloride.

In this process, the reaction between glycerol and the chlorinating agent is preferably carried out in a reactor and related ancilliary equipments made of or coated with materials resistant to chlorinating agents and in particular to hydrogen chloride under the reaction conditions. Enamelled (glass-lined) steel is a preferred vessel material. The applicant has found that such materials remain however unsatisfactory, i.e. they are corroded by liquid mixtures containing water, dichloropropanol and hydrogen chloride, resulting from the condensation of rich hydrogen chloride content vapors on the inner walls of the reactor and of related ancilliary equipments.

This aim of this invention is to provide a process for manufacturing dichloropropanol which does not exhibit that problem.

The invention therefore relates to a process for the manufacture of dichloropropanol in which glycerol is reacted with a chlorinating agent comprising hydrogen chloride, wherein, in a vessel, a liquid medium is in equilibrium with a vapor phase and wherein at least one part of the inner wall of the vessel which is above the level of the liquid medium in the vessel is maintained at a temperature lower than 120° C. or at a temperature at least 1° C. higher than the dew temperature of the vapor phase and/or is trickled with a liquid.

The part of the inner wall of the vessel which is above the level of the liquid medium in the vessel is maintained at the required temperature continuously or intermittently.

The temperature of 120° C. is the temperature at which corrosion of enamelled steel at a rate of at least 0.01 mm/year is observed in the presence of hydrogen chloride/water liquid mixtures containing at least 4% by weight of hydrogen chloride.

The vessel can be any vessel of the process for manufacturing the dichloropropanol where the temperature of the liquid phase is higher than 120° C., like for instance a reactor, a distillation column, a stripping column or a decantor.

It has now been found that by working under such conditions of temperature and/or wetting conditions the corrosion of the inner vessel wall above the level of the liquid medium can be reduced. Without wishing to be bound by any theory, it is believed that when the temperature of the inner wall of the vessel which is above the level of the liquid medium in the vessel is lower than 120° C., the corrosion rate is reduced even in contact with very corrosive condensed mixtures containing water, hydrogen chloride and dichloropropanol. It is also believed that when the temperature of the inner wall of the vessel which is above the level of the liquid medium in the vessel is at a temperature at least 1° C. higher than the dew temperature of the vapor phase above the liquid medium, the corrosion rate is reduced due to a reduced condensation of vapors containing water, hydrogen chloride and dichloropropanol. Finally, it is also believed that when the inner wall of the vessel which is above the level of the liquid medium in the vessel is trickled with a liquid, the corrosiveness of condensed mixtures containing water, hydrogen chloride and dichloropropanol is reduced by dilution. The reduction of the corrosion of the constituent materials of the vessel makes it possible to further limit the costs associated with the replacement of the latter.

In the liquid corrosive mixtures obtained by condensation of the vapors containing water, hydrogen chloride and dichloropropanol, the hydrogen chloride content is generally higher than or equal to 1% by weight of the mixture, frequently higher than or equal to 3% and often greater than or equal to 5%. The hydrogen chloride content is generally lower than or equal to 80% by weight of the mixture, frequently lower than or equal to 60% and often lower than or equal to 50%.

In the liquid corrosive mixtures obtained by condensation of the vapors containing water, hydrogen chloride and dichloropropanol, the water content is generally higher than or equal to 4% by weight of the mixture, frequently higher than or equal to 5% and often greater than or equal to 10%. The water content is generally lower than or equal to 80% by weight of the mixture, frequently lower than or equal to 70% and often lower than or equal to 60%.

In the liquid corrosive mixtures obtained by condensation of the vapors containing water, hydrogen chloride and dichloropropanol, the dichloropropanol content is generally higher than or equal to 4% by weight of the mixture, frequently higher than or equal to 5% and often greater than or equal to 10%. The dichloropropanol content is generally lower than or equal to 80% by weight of the mixture, frequently lower than or equal to 70% and often lower than or equal to 60%.

Others compounds can also be present in the liquid corrosive mixtures containing water, hydrogen chloride and dichloropropanol, like for instance glycerol, monochloropropanediol, and esters thereof.

The level of the liquid medium in the vessel is defined as the level of the liquid when the vessel is operating in stationary regime.

The inner wall of the vessel which is above the level of the liquid medium in the vessel generally extends above the level of the liquid medium in the vessel to the top of the vessel.

According to a first embodiment of the process of the invention, the temperature of the inner wall of the vessel which is above the level of the liquid medium in the vessel is at a temperature lower than 120° C., preferably lower than or equal to 110° C., more preferably lower than or equal to 100° C. and most preferably lower than or equal to 90° C.

According to a first variant of the first embodiment, the internal wall of the vessel which is above the level of the liquid medium in the vessel is cooled down by means of an external cooling system. That system can be for instance a cooling fluid circulating between the inner and outer wall of the part of the vessel (double-walled conventional jacket) which is above the level of the liquid medium in the vessel or a cooling fluid circulating in a serpentine welded on the vessel wall or connected by a thermally conductive cement or located within the protective layer (for instance serpentine flooded in the protective layer or channel drilled in the bulk of the protective layer) or a semi-shell tube (half-pipe jacket) in contact with the outer wall of the vessel which is above the level of the liquid medium in the vessel or by flushing a cooling fluid on the outer wall of the vessel which is above the level of the liquid medium in the vessel. The cooling fluid can be a gas or a liquid. It is preferred to use a gaseous fluid when flushing the outer wall. The gas can be for example dry air or nitrogen. It is preferred to use a liquid fluid when circulating in double-walled envelope and serpentines. The liquid can be an organic liquid, an inorganic liquid or a mixture thereof. It is preferred to use an inorganic liquid, more preferably water.

According to a second variant of the first embodiment, the inner wall of the vessel which is above the level of the liquid medium in the vessel is cooled down by flushing a cooling fluid on the inner wall. The fluid can be a gas or a liquid. The gas can for instance be hydrogen chloride or steam. The temperature of the gas is lower than the temperature of the liquid medium. The fluid is preferably a liquid. The liquid can be selected from a cold condensate arising from the treatment of the vapor phase in equilibrium with the liquid medium in a distillation, evaporation or stripping column, or selected from glycerol, water, an aqueous solution of hydrogen chloride, dichloropropanol, monochloropropanediol and mixtures thereof. By cold condensate, one intends to denote a condensate which temperature is lower than the temperature of the vapor phase in equilibrium with the liquid medium.

The temperature of the cooling fluid is adjusted to obtain the inner wall temperature mentioned above.

According to a second embodiment of the process of the invention, the temperature of the inner wall of the vessel which is above the level of the liquid medium in the vessel is at a temperature at least 1° C. higher than the dew temperature of the vapor above the liquid medium, preferably at least 3° C. higher, more preferably at least 5° C. higher and most preferably at least 10° C. higher.

According to a first variant of that second embodiment, the inner wall of the vessel which is above the level of the liquid medium in the vessel is heated up by means of an external heating system. That system can be for instance a heating fluid circulating between the inner and outer wall (double-walled conventional jacket) of the part of the vessel which is above the level of the liquid medium in the vessel or a heating fluid circulating in a serpentine welded to the vessel wall or connected by a thermally conductive cement or in a semi-shell tube (half-pipe jacket) in contact with the outer wall of the vessel which is above the level of the liquid medium in the vessel or by flushing a heating fluid on the outer wall of the vessel which is above the level of the liquid medium in the vessel. The heating of the part of the vessel which is above the level of the liquid medium in the vessel can also be carried out by using electric tracing or by radiation, such as electromagnetic radiations like for instance Infra Red radiations. When a heating fluid is used, it can be a gas or a liquid. When a double-walled envelope or a serpentine or a semi-shell system is used for the external heating, it is preferred to use a liquid. The liquid can be an organic, an inorganic liquid or a mixture thereof. An inorganic liquid is preferred, pressurized water being most preferred. When the heating is carried out by flushing a heating fluid, the fluid is preferably a hot gas. By hot gas, one intends to denote a gas with a temperature is higher than the temperature of the liquid medium. The gas can be nitrogen, air or steam. Steam is more preferred. Steam with a pressure lower than 10 absolute bar is the most preferred.

According to a second variant of that second embodiment, the internal wall of the vessel which is above the level of the liquid medium in the vessel is heated up by means of an internal heating system and a thermally insulating device can optionally be placed on the external wall of the vessel which is above the level of the liquid medium. The internal heating is carried out by flushing a heating fluid on the inner wall. By heating fluid, one intends to denote a fluid with a temperature higher than the temperature of the liquid medium. The fluid can for instance be nitrogen, steam, hydrogen chloride or low boiling compounds produced by the reaction between glycerol and hydrogen chloride like for instance dichloropropanol, or mixture thereof. The gas can be introduced in the vessel by any suitable way, like for instance above the level of the liquid medium in the vessel in such a way that a helicoidal stream of gas is produced above that level.

The temperature of the heating fluid is adjusted to obtain the inner wall temperature mentioned above.

Any kind of thermally insulating device can be used. Insulating material can be made of inorganic material like perlite, of organic material or mixture thereof.

According to a third embodiment of the process of the invention, the inner wall of the vessel which is above the level of the liquid medium in the vessel is trickled with a liquid. The liquid can be selected from a cold condensate arising from the treatment of the vapor phase in equilibrium with the liquid medium in a distillation, evaporation or stripping column, or selected from glycerol, water, an aqueous solution of hydrogen chloride, dichloropropanol and monochloropropanediol, and mixtures thereof. By cold condensate, one intends to denote a condensate which temperature is lower than the temperature of the vapor phase in equilibrium with the liquid medium. The liquid can be selected from another part of the process with a low concentration of hydrogen chloride.

The various embodiments which have been described above can be combined.

According to a fourth embodiment of the process of the invention, the inner wall of the vessel which is above the level of the liquid medium in the vessel, can be heated and trickled with a liquid. In that embodiment, it is preferred to heat the upper part of the inner wall and to trickle the lower of the inner wall which is above the level of the liquid medium in the vessel. The lower part generally extends from the level of the liquid medium in the vessel to 0.1 m above that level. The upper part generally extends from 0.5 m above the level of the liquid medium to the top of the vessel.

According to a fifth embodiment of the process of the invention, the inner wall of the vessel which is above the level of the liquid medium in the vessel, can be cooled and trickled with a liquid.

The examples below are intended to illustrate the invention without, however, imposing any limitation thereon.

EXAMPLE 1 (NOT ACCORDING TO THE INVENTION)

When contacted with a water-hydrogen chloride liquid mixture containing 20% by weight of hydrogen chloride at 120° C., an enamelled-lined steel sample exhibits a corrosion rate of 0.035 mm/year.

EXAMPLE 2 (ACCORDING TO THE INVENTION)

When contacted with a water-hydrogen chloride liquid mixture containing 20% by weight of hydrogen chloride at 50° C., an enamelled-lined steel sample exhibits a corrosion rate of less than 0.010 mm/year.

The invention claimed is:
1. A process comprising reacting glycerol with a chlorinating agent comprising hydrogen chloride to produce dichloropropanol in a vessel in which a liquid medium is in equilibrium with a vapour phase and according to which corrosion of at least a part of an inner vessel wall above the level of the liquid medium is at least partially avoided by cooling said inner vessel wall in order to maintain at least part of the inner vessel wall at a temperature lower than 120° C.

2. The process according to claim 1 wherein the inner vessel wall is maintained at a temperature lower than 120° C. by cooling by an external cooling system selected from a cooling fluid circulating in a serpentine or a semi-shell tube in contact with the outer wall of the vessel or by flushing a cooling fluid on the outer wall of the vessel which is above the level of the liquid medium in the vessel.

3. The process according to claim 1 wherein the inner vessel wall is maintained at a temperature lower than 120° C. by cooling by an internal cooling system which comprises flushing a cooling fluid on the inner wall of the vessel which is above the level of the liquid medium in the vessel.

4. The process according to claim 3 wherein the inner vessel wall is maintained at a temperature lower than 120° C. by cooling by an internal cooling system which consists of flushing a cooling fluid on the inner wall of the vessel which is above the level of the liquid medium in the vessel.

5. The process according to claim 1 wherein the inner vessel wall is maintained at a temperature lower than 120° C. by cooling by both :
   (a) an external cooling system selected from a cooling fluid circulating in a serpentine or a semi-shell tube in contact with the outer wall of the vessel or by flushing a cooling fluid on the outer wall of the vessel which is above the level of the liquid medium in the vessel, and
   (b) an internal cooling system which comprises flushing a cooling fluid on the inner wall of the vessel which is above the level of the liquid medium in the vessel.

6. The process according to claim 5 wherein the inner vessel wall is maintained at a temperature lower than 120° C. by cooling by both:
   (a) an external cooling system selected from a cooling fluid circulating in a serpentine or a semi-shell tube in contact with the outer wall of the vessel or by flushing a cooling fluid on the outer wall of the vessel which is above the level of the liquid medium in the vessel, and
   (b) an internal cooling system which consists of flushing a cooling fluid on the inner wall of the vessel which is above the level of the liquid medium in the vessel.

7. The process according to claim 1, further comprising subjecting at least a part of the dichloropropanol to a dehydrochlorination reaction to produce epichlorohydrin.

8. A process comprising reacting glycerol with a chlorinating agent comprising hydrogen chloride to produce dichloropropanol, and subjecting at least a part of the dichloropropanol to a dehydrochlorination reaction to produce epichlorohydrin, wherein said dichloropropanol is produced in a vessel in which a liquid medium is in equilibrium with a vapour phase and according to which corrosion of at least a part of an inner vessel wall above the level of the liquid medium is at least partially avoided by:
   (i) heating said inner vessel wall in order to maintain at least part of the inner vessel wall at a temperature at least 1° C. higher than the dew temperature of the vapour phase, or
   (ii) trickling said inner vessel wall with a liquid having a temperature which is lower than the temperature of the vapor phase, or
   (iii) trickling said inner vessel wall with a liquid having a composition that allows to dilute a condensed vapor phase, or
   (iv) combining (ii) and (v) where (v) is:
   (v) cooling said inner vessel wall in order to maintain at least part of the inner vessel wall at a temperature lower than 120° C.,
   or combining (iii) and (v),
   or combining (ii) and (iii) and (v),
   or combining (i) and (iii).

9. The process according to claim 2, wherein the inner vessel wall is maintained at a temperature lower than 120° C. by cooling by an external cooling system selected from a cooling fluid circulating in a serpentine or a semi-shell tube in contact with the outer wall of the vessel.

\* \* \* \* \*